US012008689B2

(12) United States Patent
Lu et al.

(10) Patent No.: US 12,008,689 B2
(45) Date of Patent: Jun. 11, 2024

(54) DEVICES, SYSTEMS, AND METHODS FOR DEEP-LEARNING KERNEL-BASED SCATTER ESTIMATION AND CORRECTION

(71) Applicant: CANON MEDICAL SYSTEMS CORPORATION, Tochigi (JP)

(72) Inventors: Yujie Lu, Vernon Hills, IL (US); Tzu-Cheng Lee, Mundelein, IL (US); Liang Cai, Vernon Hills, IL (US); Jian Zhou, Buffalo Grove, IL (US); Zhou Yu, Glenview, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 290 days.

(21) Appl. No.: 17/542,245

(22) Filed: Dec. 3, 2021

(65) Prior Publication Data

US 2023/0177745 A1   Jun. 8, 2023

(51) Int. Cl.
*G06V 10/00*  (2022.01)
*G06N 3/08*  (2023.01)
*G06T 11/00*  (2006.01)
*G16H 30/40*  (2018.01)

(52) U.S. Cl.
CPC ............ *G06T 11/005* (2013.01); *G06N 3/08* (2013.01); *G16H 30/40* (2018.01); *G06T 2211/40* (2013.01)

(58) Field of Classification Search
CPC ............ G06N 3/08; G06N 3/02; G06N 3/045; G06N 3/092; G06N 3/0475; G06N 3/042; G06N 3/084; G06T 11/005; G06T 11/008; G06T 2207/20081; G06T 2207/20084;
(Continued)

(56) References Cited

U.S. PATENT DOCUMENTS

| 6,256,367 | B1 | 7/2001 | Vartanian |
| 6,609,021 | B1 | 8/2003 | Fan |
| 8,135,111 | B2 | 3/2012 | Jaffray |

(Continued)

FOREIGN PATENT DOCUMENTS

| CN | 104616251 A | 5/2015 |
| CN | 105574828 A | 5/2016 |

(Continued)

OTHER PUBLICATIONS

Yang Lei et al., Male pelvic multi-organ segmentation on transrectal ultrasound using anchor-free mask CNN, Med. Phys. 48 (6), Jun. 2021.

(Continued)

*Primary Examiner* — Amir Alavi
(74) *Attorney, Agent, or Firm* — Canon U.S.A., Inc. IP Division

(57) ABSTRACT

Devices, systems, and methods obtain first radiographic-image data reconstructed based on a set of projection data acquired in a radiographic scan; apply one or more trained machine-learning models to the set of projection data and the first radiographic-image data to obtain a set of parameters for a scatter kernel; input the set of parameters and the set of projection data into the scatter kernel to obtain scatter-distribution data; and perform scatter correction on the set of projection data using the scatter-distribution data, to obtain a set of corrected projection data.

20 Claims, 10 Drawing Sheets

(58) Field of Classification Search
CPC .... G06T 2211/40; G16H 50/50; G16H 50/20; G16H 30/20; G16H 30/40
See application file for complete search history.

(56) References Cited

U.S. PATENT DOCUMENTS

| | | | |
|---|---|---|---|
| 8,483,471 | B2 | 7/2013 | Wu |
| 9,070,181 | B2 | 6/2015 | Wu |
| 9,159,124 | B2 | 10/2015 | Goshen |
| 9,480,450 | B2* | 11/2016 | Hashizume ......... A61B 6/5205 |
| 9,798,751 | B2 | 10/2017 | Birdwell |
| 10,042,079 | B2* | 8/2018 | Patnaik ................ G01V 5/22 |
| 10,115,199 | B2* | 10/2018 | Patnaik ................ G06T 7/73 |
| 10,121,267 | B2* | 11/2018 | Lin ........................ A61B 6/50 |
| 10,140,544 | B1 | 11/2018 | Zhao |
| 10,176,604 | B2* | 1/2019 | Lv ........................ G06T 7/10 |
| 10,446,262 | B2 | 10/2019 | Fält |
| 10,542,944 | B2 | 1/2020 | Petersilka |
| 10,593,070 | B2 | 3/2020 | Lu |
| 10,734,116 | B2 | 8/2020 | Chen |
| 10,937,206 | B2 | 3/2021 | Lu |
| 10,970,887 | B2 | 4/2021 | Wang |
| 11,182,895 | B2 | 11/2021 | Honkala |
| 11,562,482 | B2* | 1/2023 | Morgas ................ G06T 7/12 |
| 11,605,186 | B2* | 3/2023 | Shea .................... A61B 6/06 |
| 11,633,163 | B2* | 4/2023 | De Man ............ G06T 11/006 378/7 |
| 11,662,321 | B2* | 5/2023 | Rothe ................. A61B 6/5282 378/19 |
| 11,854,123 | B2* | 12/2023 | Bai ...................... A61B 6/027 |
| 2003/0136894 | A1* | 7/2003 | Gerlach ............... H04N 1/0281 250/201.1 |
| 2014/0153691 | A1 | 6/2014 | Kurochi |
| 2018/0018757 | A1 | 1/2018 | Suzuki |
| 2018/0330233 | A1 | 11/2018 | Rui |
| 2019/0066268 | A1 | 2/2019 | Song |
| 2019/0104940 | A1 | 4/2019 | Zhou |
| 2019/0197740 | A1 | 6/2019 | Lu |
| 2020/0234471 | A1 | 7/2020 | Lu |
| 2020/0273214 | A1 | 8/2020 | Xu |
| 2020/0279410 | A1 | 9/2020 | Lee |
| 2020/0340932 | A1 | 10/2020 | Lu |
| 2021/0003652 | A1 | 1/2021 | Zeller |
| 2021/0007695 | A1 | 1/2021 | Lu |
| 2021/0059625 | A1 | 3/2021 | Bai |
| 2021/0121149 | A1 | 4/2021 | Manhart |
| 2021/0192809 | A1 | 6/2021 | Paysan |
| 2021/0282732 | A1 | 9/2021 | Qi |
| 2023/0177745 | A1* | 6/2023 | Lu ........................ G16H 50/50 382/131 |

FOREIGN PATENT DOCUMENTS

| | | |
|---|---|---|
| CN | 110197516 A | 9/2019 |
| CN | 110660111 A | 1/2020 |
| CN | 111325686 A | 6/2020 |
| CN | 113096211 A | 7/2021 |
| CN | 113256753 A | 8/2021 |
| KR | 20200059712 A | 5/2020 |
| WO | 2021004157 A1 | 1/2021 |

OTHER PUBLICATIONS

Ernst-Peter Rührnschopf et al., A general framework and review of scatter correction methods in x-ray cone-beam computerized tomography. Part 1: Scatter compensation approaches, Jun. 2011.

Ernst-Peter Rührnschopf et al., A general framework and review of scatter correction methods in cone beam CT. Part 2: Scatter estimation approaches, Aug. 2011.

M Sun et al., Improved scatter correction using adaptive scatter kernel superposition, Phys. Med. Biol. 55 (2010) 6695-6720, Oct. 2010.

Yu Zou et al., A Physics-based Fast Approach to Scatter Correction for Large Cone Angle Computed Tomographic Systems, 2011 IEEE Nuclear Science Symposium Conference Record, Nov. 2011.

Wojciech Zbijewski et al., Efficient Monte Carlo Based Scatter Artifact Reduction in Cone-Beam Micro-CT, IEEE Transactions on Medical Imaging, vol. 25, No. 7, Jul. 2006.

Mingshan Sun et al., Rapid Scatter Estimation for CBCT using the Boltzmann Transport Equation, Medical Imaging 2014: Physics of Medical Imaging, Mar. 2014.

Weiguang Yao et al., An analytical approach to estimating the first order x-ray scatter in heterogeneous medium, Med. Phys. 36 (7), Jun. 2009.

Shiyu Xu et al., Deep residual learning in CT physics: scatter correction for spectral CT, Nov. 2017.

Joscha Maier et al., Deep scatter estimation (DSE): feasibility of using a deep convolutional neural network for realtime x-ray scatter prediction in conebeam CT, Proc. SPIE 10573, Medical Imaging 2018: Physics of Medical Imaging, 105731L, Mar. 2018.

Yangkang Jiang et al., Scatter correction of cone-beam CT using a deep residual convolution neural network (DRCNN), Phys. Med. Biol. 64 (2019), Jul. 2019.

Hua Qian et al., Deep Learning Models for PET Scatter Estimations, 2017 IEEE Nuclear Science Symposium and Medical Imaging Conference (NSS/MIC), Oct. 2017.

* cited by examiner

DEVICES, SYSTEMS, AND METHODS FOR DEEP-LEARNING KERNEL-BASED SCATTER ESTIMATION AND CORRECTION

BACKGROUND

Technical Field

This application generally concerns machine learning and artificial neural networks for scatter estimation in radiographic imaging.

Background

Radiographic imaging can produce (e.g., reconstruct) images of an object's internal structures, such as the internal members of a patient's body. For example, computed tomography (CT) scans use multiple X-ray images of an object, which were taken from different angles, to reconstruct volume images of the interior of the object. However, X-ray scatter can degrade the quality of reconstructed images.

SUMMARY

Some embodiments of an imaging-data-processing method comprise obtaining first radiographic-image data reconstructed based on a set of projection data acquired in a radiographic scan; applying one or more trained machine-learning models to the set of projection data and the first radiographic-image data to obtain a set of parameters for a scatter kernel; inputting the set of parameters and the set of projection data into the scatter kernel to obtain scatter-distribution data; and performing scatter correction on the set of projection data using the scatter-distribution data, to obtain a set of corrected projection data.

Some embodiments of a method comprise obtaining a training dataset for a scatter model, wherein the training dataset includes projection data, radiographic-image data, and target data, wherein the target data define a scatter distribution, and wherein the scatter model accepts, as inputs, a set of parameters and projection data; applying the projection data and the radiographic-image data to one or more machine-learning models to generate the set of parameters for the scatter model; using the scatter model to generate, based on the set of parameters and on the projection data, output scatter-distribution data; applying the output scatter-distribution data and the target data to a loss function to obtain a loss value; and updating the one or more machine-learning models based on the loss value.

Some embodiments of a device comprise one or more computer-readable storage media and one or more processors. The one or more processors cooperate with the one or more computer-readable storage media to cause the device to obtain first radiographic-image data reconstructed based on a set of projection data acquired in a radiographic scan; apply one or more trained machine-learning models to the set of projection data and the first radiographic-image data to obtain a set of parameters for a scatter model; apply the scatter model, using the set of parameters and the set of projection data as inputs, to obtain scatter-distribution data; and perform scatter correction on the set of projection data using the scatter-distribution data, to obtain a set of corrected projection data.

DESCRIPTION

Figure 1A:
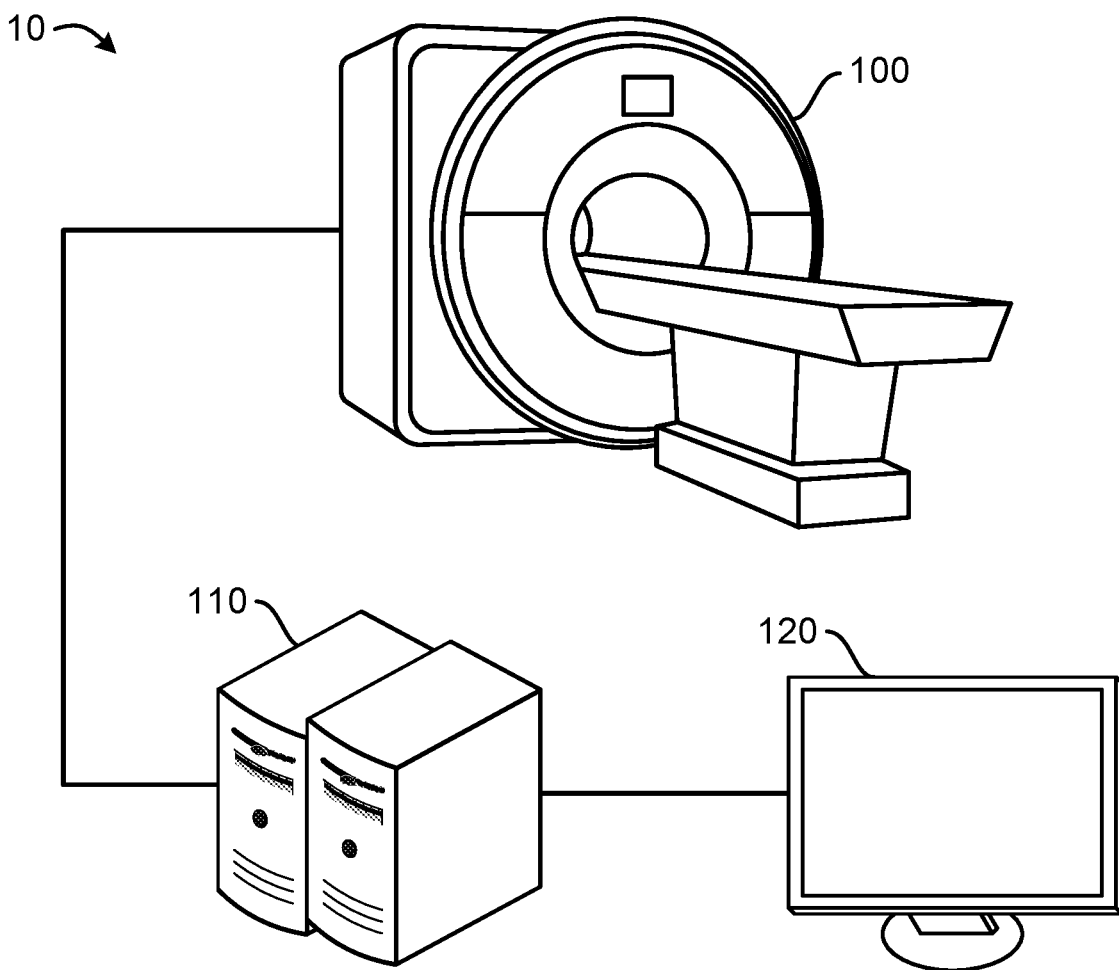
FIG. 1A illustrates an example embodiment of a medical-imaging system.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein. Furthermore, some embodiments include features from two or more of the following explanatory embodiments.

Also, as used herein, the conjunction "or" generally refers to an inclusive "or," although "or" may refer to an exclusive "or" if expressly indicated or if the context indicates that the "or" must be an exclusive "or." Furthermore, as used herein, the terms "first," "second," and so on, do not necessarily denote any ordinal, sequential, or priority relation, but are used to more clearly distinguish one member, operation, element, group, collection, set, etc. from another, unless specified otherwise.

And in the following description and in the drawings, like reference numerals designate identical or corresponding members throughout the several views.

FIG. 1A illustrates an example embodiment of a medical-imaging system 10. The medical-imaging system 10 includes at least one scanning device 100; one or more image-generation devices 110, each of which is a specially-configured computing device (e.g., a specially-configured desktop computer, a specially-configured laptop computer, a specially-configured server); and a display device 120.

The scanning device 100 is configured to acquire projection data by performing a radiographic scan of a region (e.g., area, volume, slice) of a subject (e.g., a patient), and the region of the subject may include one or more objects (e.g., organs, vessels). The scanning modality of the radiographic scan may be, for example, computed tomography (CT), positron emission tomography (PET), X-ray radiography, and tomosynthesis.

The one or more image-generation devices 110 obtain projection data from the scanning device 100 and generate radiographic-image data that define a reconstruction of the scanned region based on the projection data. Also, the reconstruction includes one or more reconstructed images of the scanned region. To generate the radiographic-image data, for example when the projection data include groups of projection data that were acquired at different angles or positions, the one or more image-generation devices 110 perform a reconstruction process on the projection data. Examples of reconstruction processes include filtered back projection (e.g., Radon transform) and iterative reconstruction.

After the one or more image-generation devices 110 generate the reconstruction of the scanned region, the one or more image-generation devices 110 send the reconstruction to the display device 120, which displays one or more reconstructed images from the reconstruction.

Figure 1B:
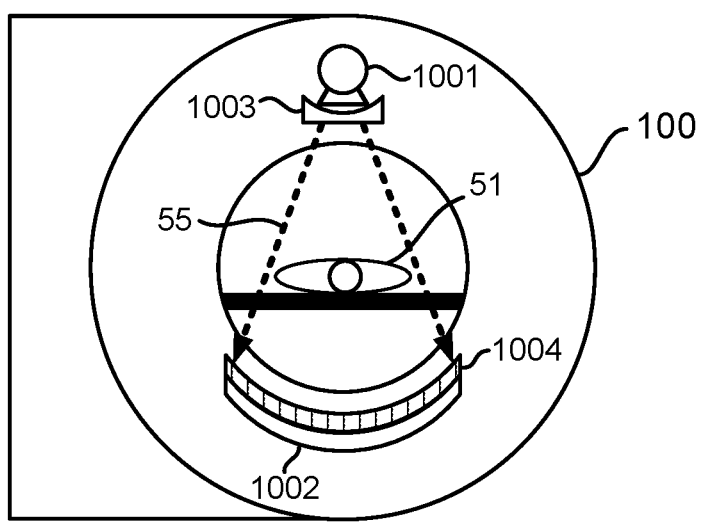
FIG. 1B illustrates an example embodiment of a scanning device.

FIG. 1B illustrates an example embodiment of a scanning device 100. The scanning device 100 includes a radiation emitter 1001 and a radiation detector 1002, which are positioned on opposite sides of a subject 51, as well as a bowtie filter 1003. The radiation emitter 1001 emits radiation 55 (e.g., X-rays) that travels through a scanned region of the subject 51 and is detected by the radiation detector 1002. The radiation detector 1002 generates projection data 1010 (e.g., groups of projection data 1010) based on the detected radiation 55. In this embodiment, the radiation emitter 1001 emits the radiation in the form of a tapering beam (e.g., a rectangular pyramid, a square pyramid, a circular cone, an elliptical cone). Additionally, the radiation detector 1002 has a curved detection surface. But, in some embodiments, the radiation emitter 1001 emits the radiation in the form of parallel beams, or the radiation detector 1002 has a flat detection surface.

Figure 2:
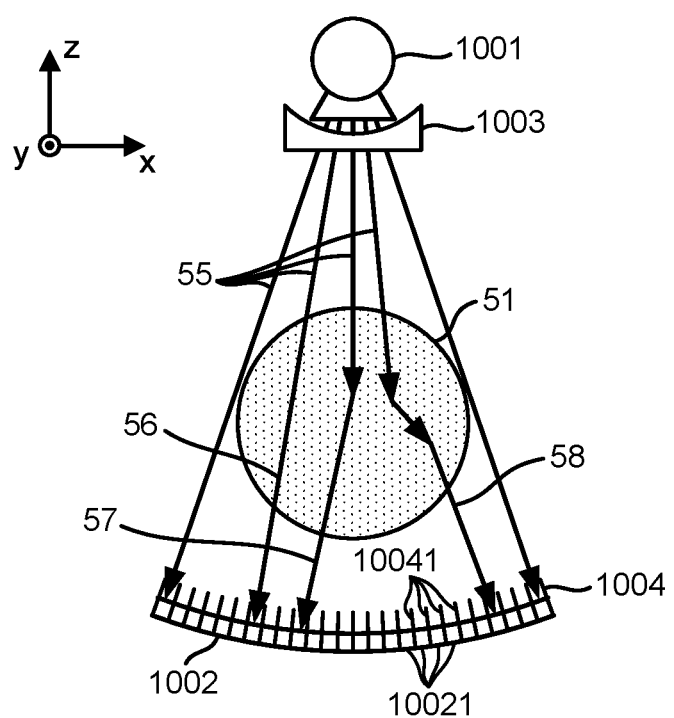
FIG. 2 illustrates an example embodiment of scattering.

Additionally, this embodiment includes a collimator device 1004, which is positioned on or near a detection-surface side of the radiation detector 1002. As shown in FIG. 2, the collimator device 1004 includes a plurality of collimator plates 10041. The collimator plates 10041 are provided in such a manner that their plate surfaces extend parallel to a radiation direction of the radiation 55 that is emitted by the radiation emitter 1001. Furthermore, the collimator plates 10041 may be located on the boundaries of the detecting elements 10021 (e.g., pixels) of the radiation detector 1002.

Also, in this embodiment, the radiation emitter 1001 and the radiation detector 1002 are configured to rotate around the subject 51. Thus, at different angles relative to the subject 51, the radiation emitter 1001 emits radiation 55 that travels through the scanned region of the subject 51 and is detected by the radiation detector 1002. And, at each of the angles, the radiation detector 1002 generates a respective group of projection data 1010. The angles collectively define an angular scanning range. For example, in some embodiments, the angular scanning range is 0 to 180°, and in some embodiments the angular scanning range is 0 to 360°. Additionally, some embodiments of the scanning device 100 generate respective groups of projection data at 900 to 1,200 angles. Thus, for example, if the scanning device generates groups of projection data at 900 angles that range from 0 to 180° and that are evenly spaced, then the increment between angles would be 0.2°. Also for example, if the scanning device generates groups of projection data at 1,200 angles that range from 0 to 360° and that are evenly spaced, then the increment between angles would be 0.3°.

As the beams of radiation travel through the subject 51, some of the radiation may be scattered. For example, FIG. 2 illustrates an example embodiment of scattering. The radiation 55 includes a primary flux 56, which includes the radiation (e.g., X-rays) that has not been scattered. In addition to the primary flux 56, the radiation 55 also includes a first-scatter flux 57, which includes the radiation (the rays of radiation) that has undergone a single scattering event. And the radiation 55 also includes a multi-scatter flux 58 (which may be referred to as multiple-scatter flux), which includes the radiation (the rays of radiation) that has been scattered multiple times. The radiation detector 1002 can detect the total flux T(u, v), which includes both the primary flux 56 (P(u, v)) and the scatter flux S(u, v) (which includes the first-scatter flux 57 and the multi-scatter flux 58). The scatter flux S(u, v) may be described or otherwise defined by scatter-distribution data. And the rays of radiation in the scatter flux S(u, v) may be referred to herein as "scatter rays."

Because the collimator plates 10041 extend in, or approximately in, the z-axis direction, the scatter rays that traverse (have a directional component that is perpendicular to) the z-axis direction can be blocked by the collimator device 1004. However, scatter rays that advance along the z-axis direction (have no directional component that is perpendicular to the z-axis direction or have a small directional component that is perpendicular to the z-axis direction) cannot be blocked by the collimator device 1004. Thus, the scatter flux S(u, v) may include scatter rays that advance along the z-axis direction and may not include scatter rays that traverse the z-axis direction.

In radiographic imaging, scattered radiation that is detected by the radiation detector 1002 can reduce image quality. For example, scattered X-rays in computed tomography (CT) (e.g., cone-beam CT with a wide-beam geometry) can negatively affect the rapid and accurate generation of high-quality (e.g., scatter-free) reconstructed images. Inefficient scatter simulation and compensation can affect image quality, resulting in poor image contrast, artifacts, and other errors in CT image reconstruction. To correct for detected scatter rays in the total flux and isolate the primary flux, the measured projection data (the total flux) can be used to first estimate the scatter flux (e.g., as described by the scatter distribution), and then the estimated scatter flux can be removed from the total flux, leaving the primary flux.

Scatter models (e.g., scatter kernels, such as convolutional kernels) can be used to calculate the scatter distribution (the scatter flux S(u, v)). Also, some scatter models account for the first-scatter flux and the multi-scatter flux. The scatter distribution depends on variables that include the shapes of the objects in the scanned region, the distributions of the objects in the scanned region, and the materials that compose the objects. For example, in certain medical contexts, the scatter distribution can depend on a patient's shape and on the distribution of the patient's organs within the patient. Various embodiments of scatter models can account for some or all of these variables, but the accuracy of these scatter models may be reduced if their parameters 1103 are not accurate.

Some embodiments of scatter models are double-Gaussian kernel models, such as the following double-Gaussian kernel model:

$$G_0(c,r) = Z_R^2 G_R + Z_c G_c = Z_R^2 e^{-(\beta_R u^2 + \alpha_R v^2)} + Z_c e^{-(\beta_c u^2 + \alpha_c v^2)}. \quad (1)$$

This double-Gaussian kernel model $G_0(c, r)$ combines the Rayleigh and Compton scatter kernels with multiplication of the first Rayleigh parameter $Z_R$ and the Compton parameter $Z_c$. $Z_R$ and $Z_c$ depend on the equivalent monochromatic energy (E) and the material of the scanned object. The parameters $\beta_R$, $\alpha_R$, $\beta_c$, and $\alpha_c$ depend not only on scanned geometry, equivalent monochromatic energy, and the anti-scatter grid used, but also on the Rayleigh parameter of the scanned object. (c, r) are column and row indices of a detector pixel in projections and (u, v) are the coordinate distances relative to the center of the detector. Therefore, $Z_R$, $Z_c$, $\beta_R$, $\alpha_R$, $\beta_c$, and $\alpha_c$ are adjustable parameters. Also, other scatter models that have adjustable parameters can be used.

Figure 3:
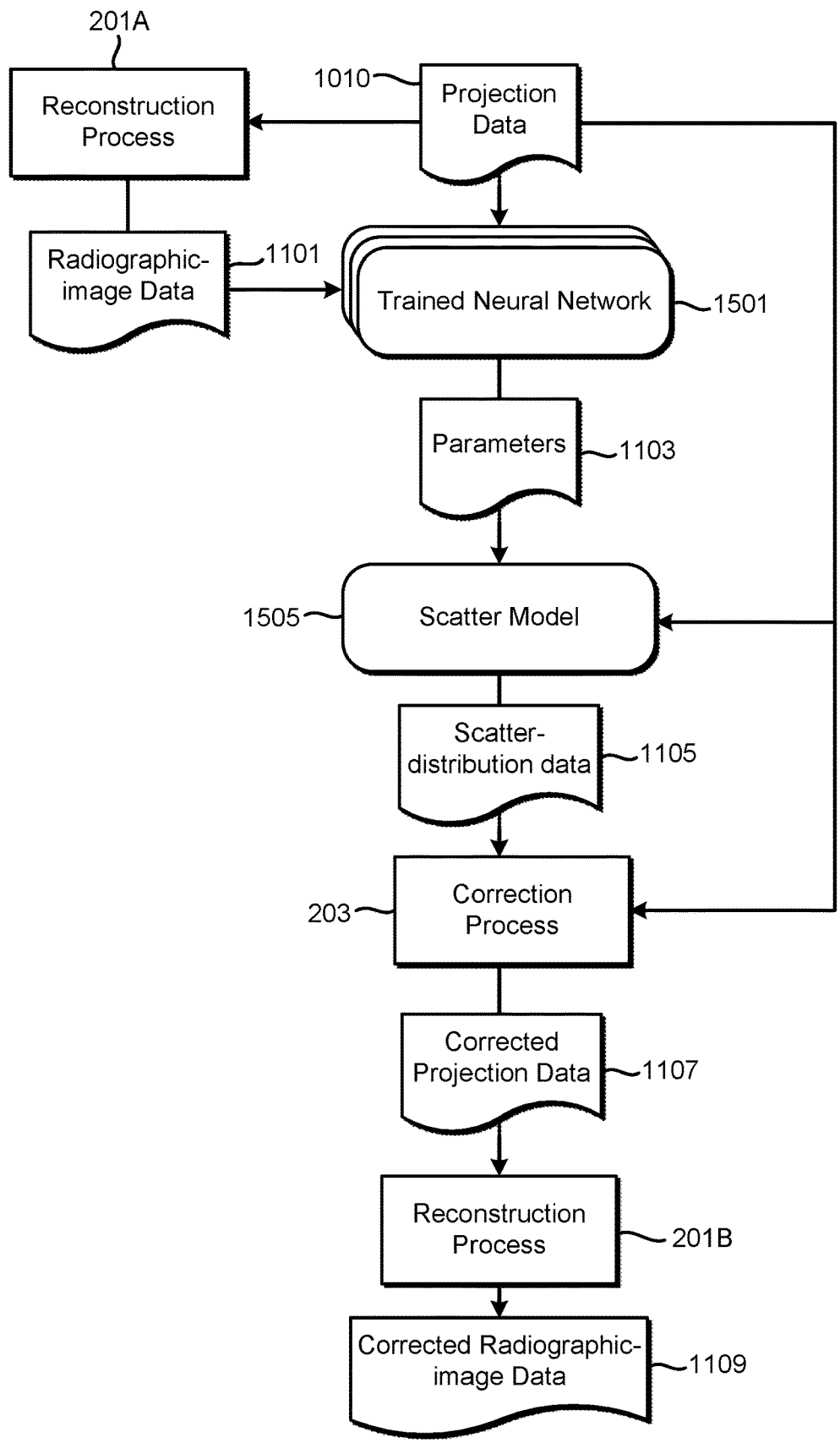
FIG. 3 illustrates the flow of information in an example embodiment of an image-reconstruction process.

FIG. 3 illustrates the flow of information in an example embodiment of an image-reconstruction process. Projection data 1010 (e.g., CT projection data) are input into a first reconstruction process 201A, which generates radiographic-image data 1101 (first radiographic-image data) based on the projection data 1010. The radiographic-image data 1101 define one or more reconstructed images of the scanned region, and the projection data 1010 may include sets of projection data 1010 that were acquired at different angles or positions. Examples of reconstruction processes include filtered back projection (e.g., Radon transform) and iterative reconstruction.

One or more trained neural networks 1501 are applied using the radiographic-image data 1101 and the projection data 1010 as inputs, and the one or more trained neural networks 1501 output parameters 1103 for a scatter model 1505 (e.g., scatter kernel, which may also be referred to as a physical-scatter kernel). Also, the one or more trained neural networks 1501 may output parameters 1103 that are optimized for scatter rays that advance along the z-axis direction, which cannot be blocked by the collimator plates 10041 that extend in the z-axis direction. The one or more trained neural networks 1501 may extract features from both the radiographic-image data 1101 and the projection data 1010 and generate the parameters 1103 based on the features. For example, the one or more trained neural networks 1501 may extract a patient's shape and organ distribution from the radiographic-image data 1101 and extract photon-absorption information from the projection data 1010, which may improve the accuracy of the parameters 1103. Also, for example, the one or more trained neural networks 1501 may include one or more of the following: multilayer perceptron neural networks, convolutional neural networks, deep stacking neural networks, recurrent neural networks, and modular neural networks.

In embodiments that include only one trained neural network 1501, the one trained neural network 1501 may output all of the parameters 1103. In embodiments that include multiple trained neural networks 1501, each of the trained neural networks 1501 may output a respective subset of the parameters 1103, and the subsets may not overlap (i.e., each parameter 1103 is output by one, and only one, of the trained neural networks 1501).

The scatter model 1505 is then applied using the parameters 1103 and the projection data 1010 as inputs, and the scatter model 1505 outputs scatter-distribution data 1105, which define respective scatter distributions (e.g., the scatter flux S(u, v)) for some or all of the projection data 1010. Thus, the scatter-distribution data 1105 may define a total scatter distribution for all the projection data 1010. For example, if the projection data 1010 include sets of projection data 1010 (e.g., sets that were acquired at different angles or positions), then the scatter-distribution data 1105 may define respective scatter distributions for each of the sets, and the combination of all of the scatter-distribution data 1105 may define the total scatter distribution for all the projection data 1010.

The scatter-distribution data 1105 and the projection data 1010 are then input into a correction process 203, which corrects the projection data 1010 based on the scatter-distribution data 1105, thereby producing corrected projection data 1107, in which the scatter has been reduced or eliminated. The corrected projection data 1107 are then input to a second reconstruction process 201B, which may be the same as the first reconstruction process 201A or different from the first reconstruction process 201A. The second reconstruction process 201B generates corrected radiographic-image data 1109 (second radiographic-image data) based on the corrected projection data 1107. The corrected radiographic-image data 1109 define one or more reconstructed images of the scanned region.

Figure 4:
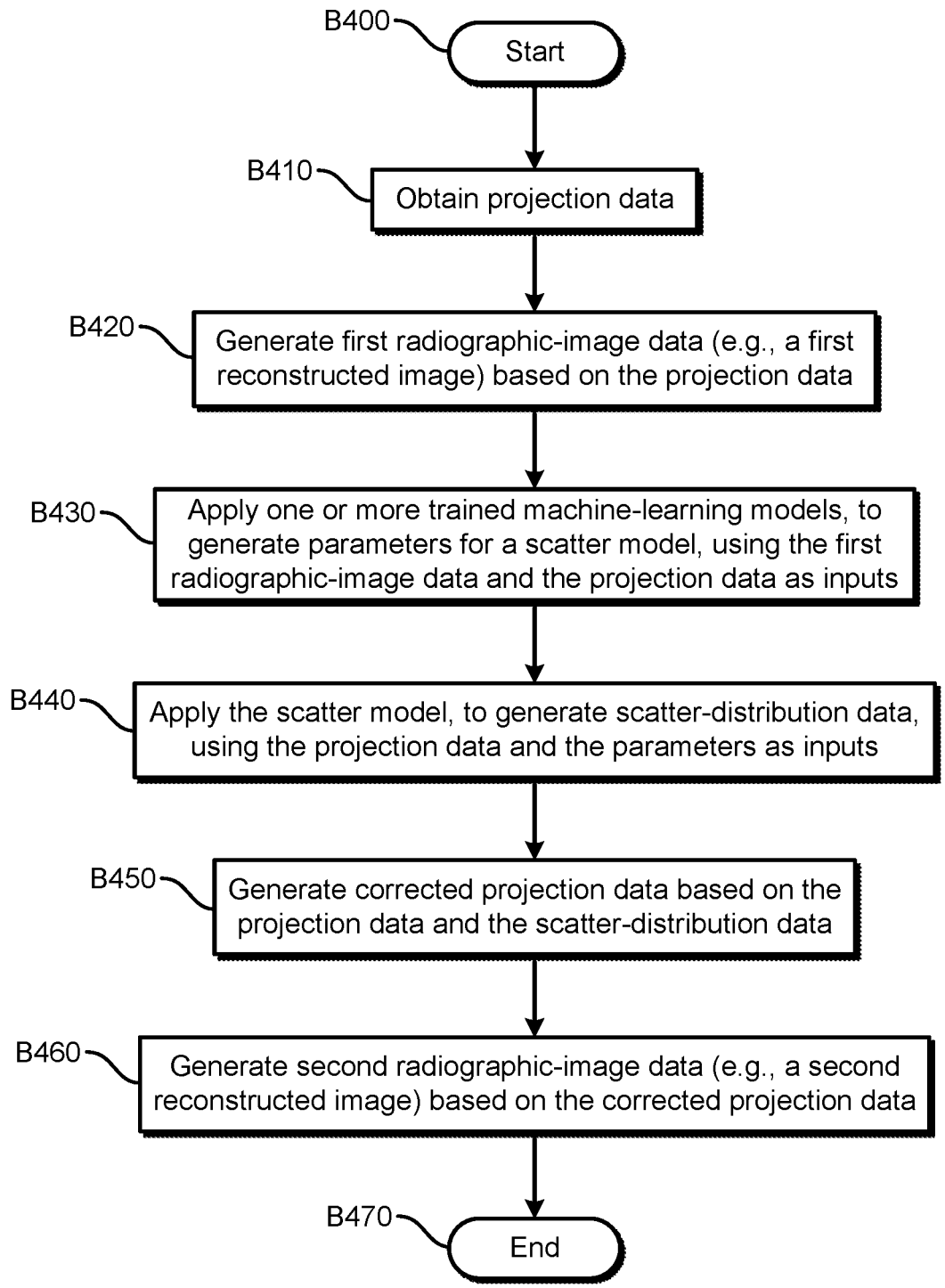
FIG. 4 illustrates an example embodiment of an image-reconstruction process.

FIG. 4 illustrates an example embodiment of an image-reconstruction process. Although this operational flow and the other operational flows that are described herein are each presented in a certain order, some embodiments may perform at least some of the operations in different orders than the presented orders. Examples of different orders include concurrent, parallel, overlapping, reordered, simultaneous, incremental, and interleaved orders. And some embodiments of the operational flows may include blocks from two or more of the operational flows that are described herein. Thus, other embodiments of the operational flows that are described herein may omit blocks, add blocks, change the order of the blocks, combine blocks, or divide blocks into more blocks.

Furthermore, although the operational flows that are described herein are performed by an image-generation device, some embodiments of these operational flows are performed by two or more image-generation devices or by one or more other specially-configured computing devices.

The flow starts in block B400 and moves to block B410, where an image-generation device obtains projection data (e.g., sets of projection data). The projection data may be obtained from one or more scanning devices or from devices (e.g., external storage devices, such as network-connected storage devices) that store the projection data.

Next, in block B420, the image-generation device generates first radiographic-image data based on the projection data. The first radiographic-image data define a first reconstructed image.

The flow then moves to block B430, where the image-generation device applies one or more trained machine-learning models, to generate parameters for a scatter model, using the first radiographic-image data and the projection data as inputs. Then, in block B440, the image-generation device applies the scatter model, to generate scatter-distribution data, using the projection data and the parameters as inputs.

The flow then proceeds to block B450, where the image-generation device generates corrected projection data based on the projection data and on the scatter-distribution data. For example, the image-generation device may subtract (or otherwise remove) the scatter-distribution data from the projection data. Thus, the image-generation device can subtract the scatter flux S(u, v) (which is defined by the scatter-distribution data) from the total flux T(u, v) (which is described by the projection data) to obtain the primary P(u, v) flux (which is described by the corrected projection data).

The flow then advances to block B460, where the image-generation device generates second radiographic-image data (corrected radiographic-image data), which define one or more second reconstructed images (one or more corrected reconstructed images), based on the corrected projection data. Also, the image-generation device may display the one or more second reconstructed images on a display device.

Finally, the flow ends in block B470.

Figure 5:
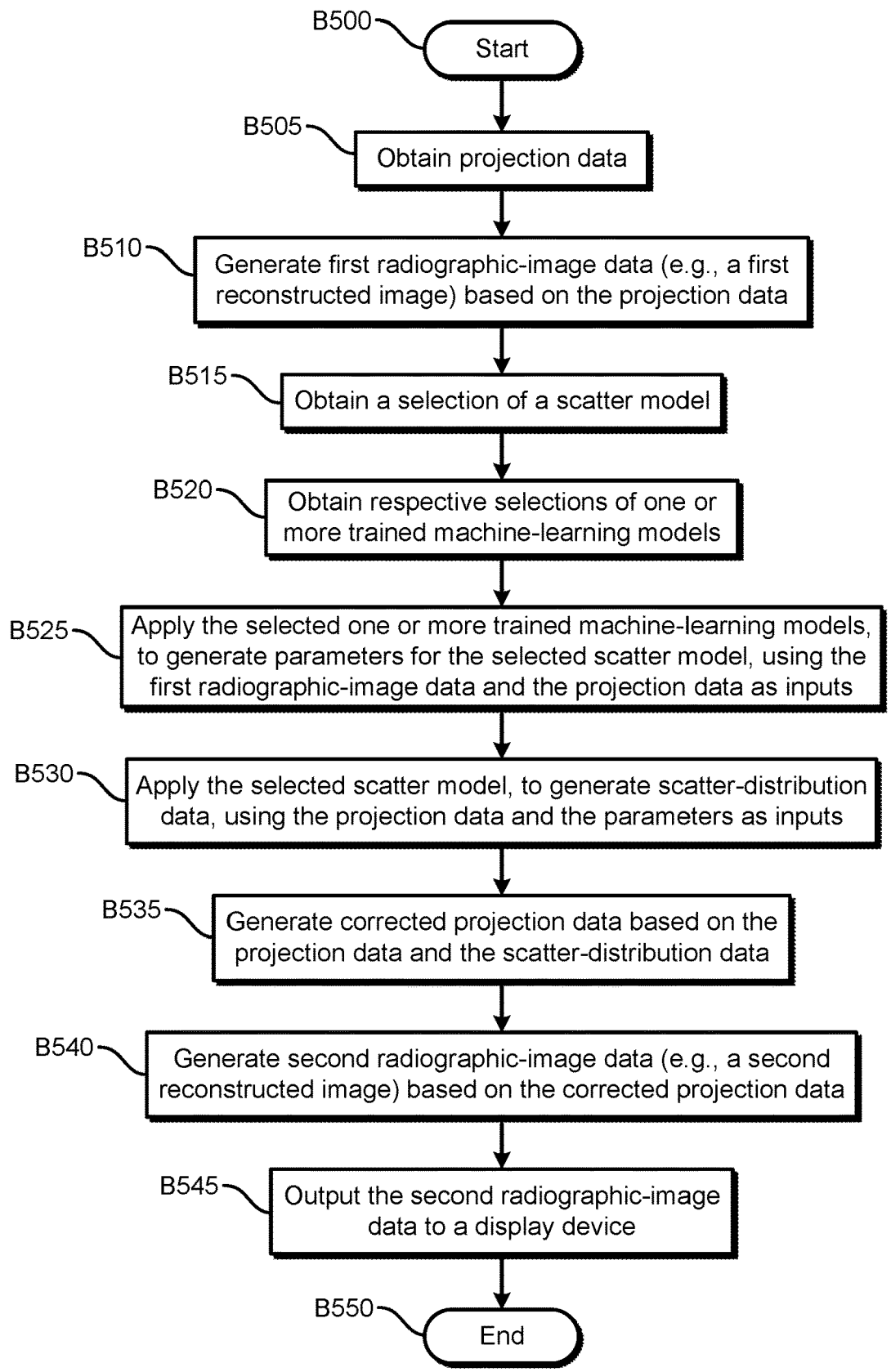
FIG. 5 illustrates an example embodiment of an image-reconstruction process.

FIG. 5 illustrates an example embodiment of an image-reconstruction process. The flow starts in block B500 and moves to block B505, where an image-generation device obtains projection data (e.g., sets of projection data). The projection data may be obtained from one or more scanning devices or from devices that store the projection data. Next, in block B510, the image-generation device generates first radiographic-image data (e.g., one or more first reconstructed images) based on the projection data.

The flow then moves to block B515, where the image-generation device obtains a selection of a scatter model. For example, the image-generation device may obtain the selection from a user input, or the image-generation device may generate the selection. In embodiments where the image-generation device generates the selection, the generation of the selection may be based on the projection data or the first radiographic-image data.

Next, in block B520, the image-generation device obtains respective selections of one or more trained machine-learning models. For example, the image-generation device may obtain the respective selections from user inputs, or the image-generation device may generate the respective selections. In embodiments where the image-generation device generates the respective selections, the generation of the respective selections may be based on the projection data, the first radiographic-image data, or the selected scatter model.

The flow then moves to block B525, where the image-generation device applies the selected one or more trained machine-learning models, to generate parameters for the selected scatter model, using the first radiographic-image data and the projection data as inputs. Then, in block B530, the image-generation device applies the selected scatter model, to generate scatter-distribution data, using the projection data and the parameters as inputs.

The flow then proceeds to block B535, where the image-generation device generates corrected projection data based on the projection data and on the scatter-distribution data. The flow then advances to block B540, where the image-generation device generates second radiographic-image data (corrected radiographic-image data), which define one or more second reconstructed images (one or more corrected reconstructed images), based on the corrected projection data. Next, in block B545, the image-generation device outputs the second radiographic-image data to a display device.

Finally, the flow ends in block B550.

Figure 6:
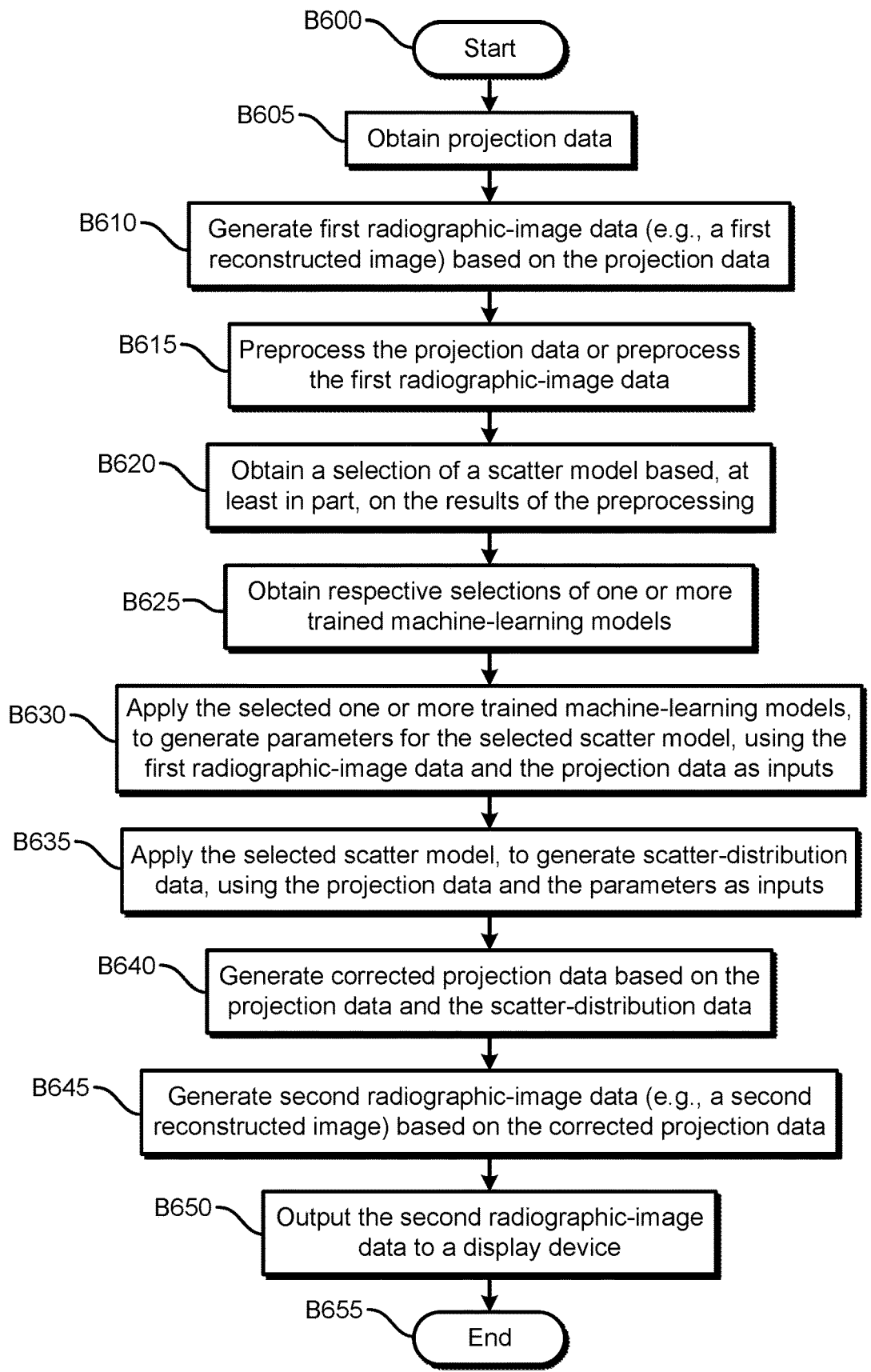
FIG. 6 illustrates an example embodiment of an image-reconstruction process.

FIG. 6 illustrates an example embodiment of an image-reconstruction process. The flow starts in block B600 and moves to block B605, where an image-generation device obtains projection data (e.g., sets of projection data). The projection data may be obtained from one or more scanning devices or from devices that store the projection data. Next, in block B610, the image-generation device generates first radiographic-image data based on the projection data.

The flow then proceeds to block B615, where the image-generation device preprocess the projection data or preprocesses the first radiographic-image data. In some embodiments, the preprocessing extracts one or more features from the projection data or the first radiographic-image data. For example, the preprocessing may extract the shapes and the positions of objects (e.g., organs) in the scanned region and may identify the materials or the properties of the materials in the scanned region. Furthermore, the preprocessing may fit the data to one or more trained machine-learning models (or to one or more scatter models, as shown in FIG. 7).

Figure 7:
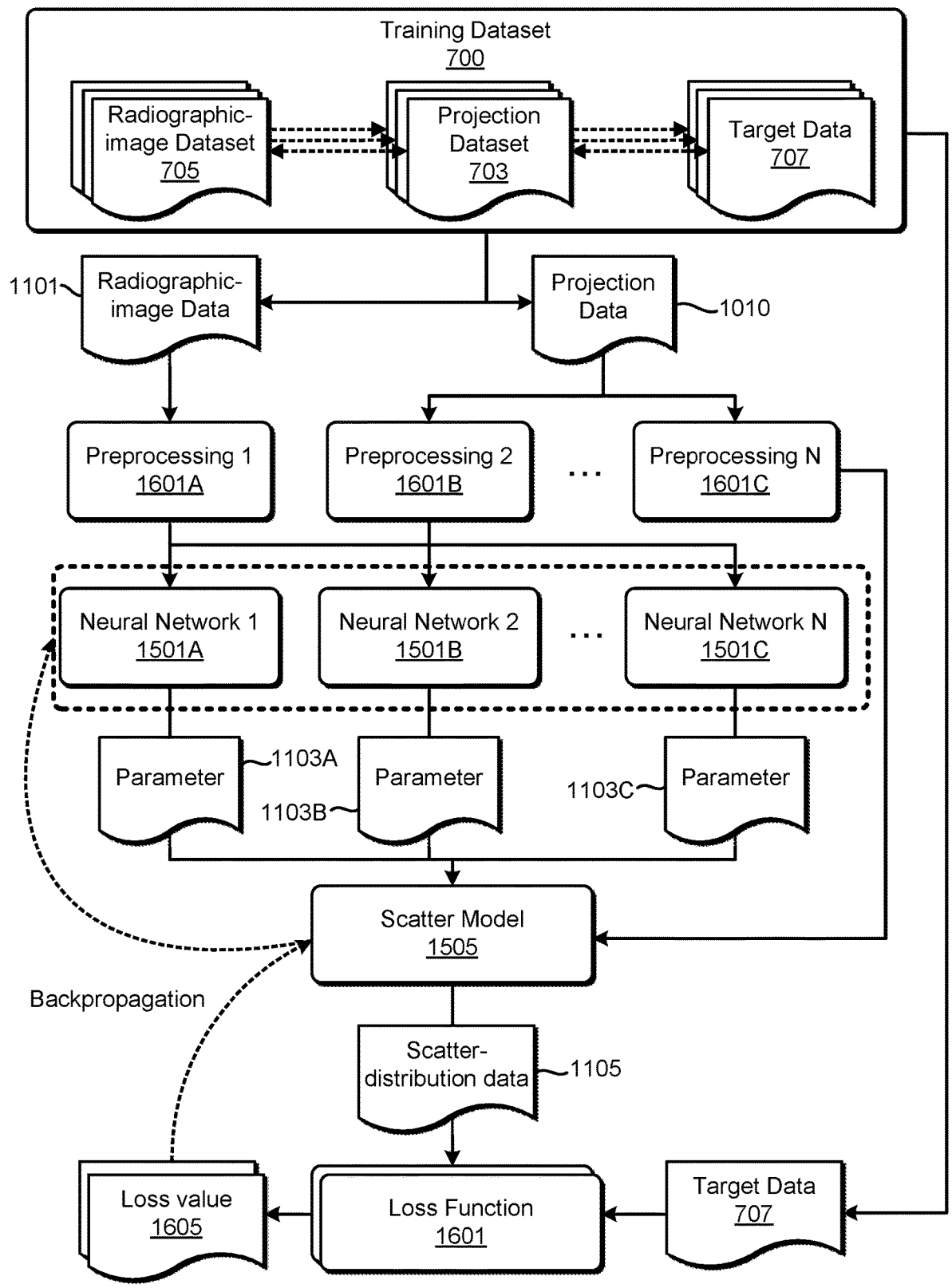
FIG. 7 illustrates the flow of information in an example embodiment of a training process.
Figure 8:
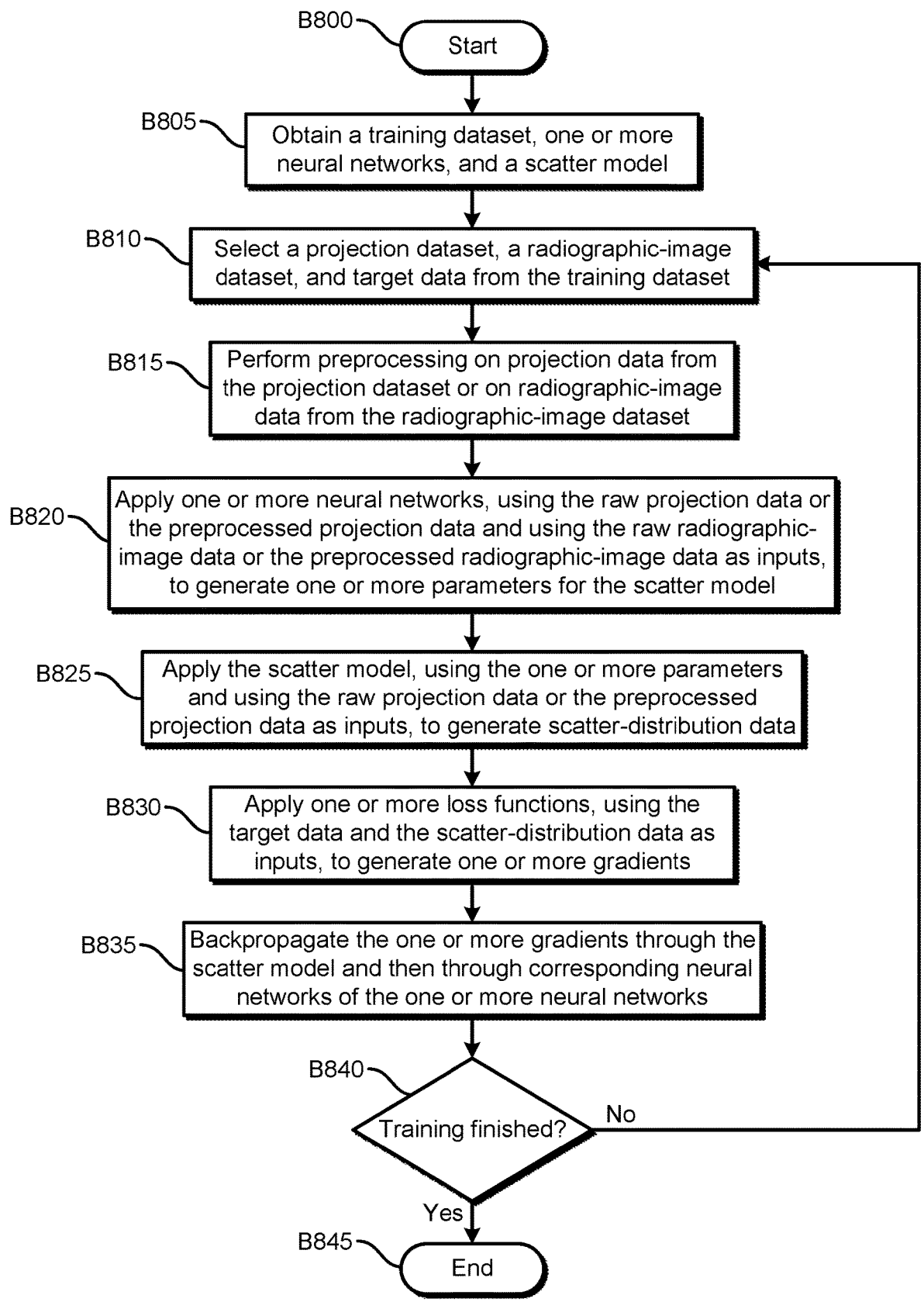
FIG. 8 illustrates an example embodiment of a neural-network training process.
Figure 9:
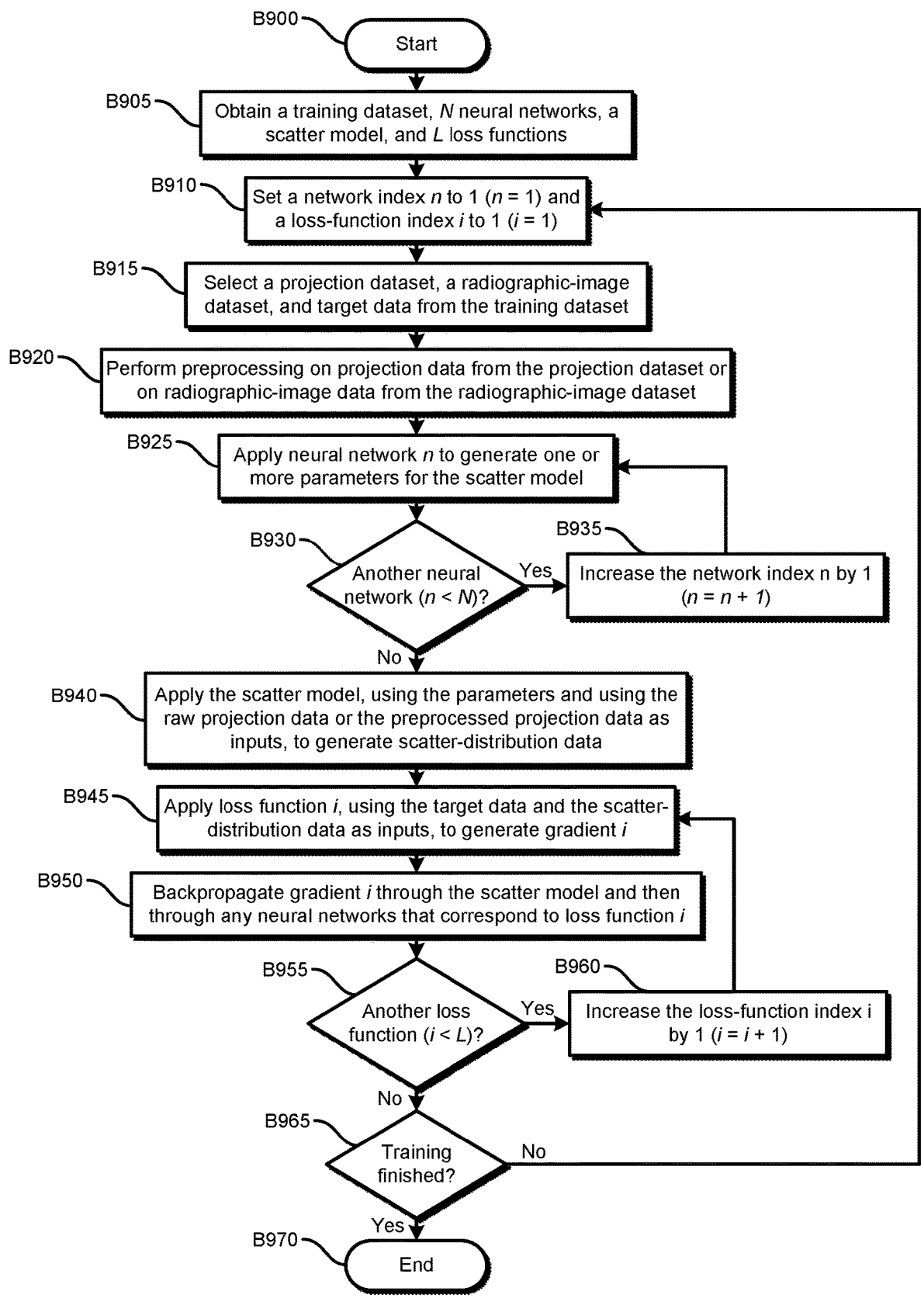
FIG. 9 illustrates an example embodiment of a neural-network training process.

Projection data and radiographic-image data that have not been preprocessed for a machine-learning model and have not been preprocessed for a scatter model (e.g., projection data that have not been processed in any of block B615 in FIG. 6, block B815 in FIG. 8, block B920 in FIG. 9, and preprocessing 1 (1601A) to preprocessing N (1601C) in FIG. 7) may be referred to herein as raw projection data and raw radiographic-image data. Although raw projection data and raw radiographic-image data have not been subjected to preprocessing either for a machine-learning model or for a scatter model (e.g., as performed in block B615), raw projection data and raw radiographic-image data may have been subjected to other processing that is applied to digital signals. For example, raw projection data may have been subjected to sensor offset correction and log conversion. Also for example, raw projection data and raw radiographic-image data may have been subjected to calibration, beam hardening correction, ring artifact correction, and noise reduction.

The flow then moves to block B620, where the image-generation device obtains a selection of a scatter model based, at least in part, on the results of the preprocessing in block B615. For example, the image-generation device may generate the selection based on the shapes and the positions of objects in the scanned region or based on the materials or the properties of the materials in the scanned region. Also, the image-generation device may generate a list of scatter models based on the shapes and the positions of the objects in the scanned region or based on the materials or the properties of the materials in the scanned region, present the list to a user, and receive a selection of a scatter model in the list from the user.

Next, in block B625, the image-generation device obtains respective selections of one or more trained machine-learning models. For example, the image-generation device may obtain the respective selections from user inputs, or the image-generation device may generate the respective selections. In embodiments where the image-generation device generates the respective selections, the generation of the respective selections may be based on the projection data, the first radiographic-image data, the preprocessing that was performed in block B615, or the selected scatter model.

The flow then moves to block B630, where the image-generation device applies the selected one or more trained machine-learning models, to generate parameters for the selected scatter model, using the first radiographic-image data and the projection data as inputs. If the projection data was preprocessed in block B615, then the preprocessed projection data may be used as inputs to the selected one or more trained machine-learning models. And, if the first radiographic-image data was preprocessed in block B615, then the preprocessed first radiographic-image data may be used as inputs to the selected one or more trained machine-learning models. Also, some embodiments use the raw first radiographic-image data or the raw projection data as inputs. Then, in block B635, the image-generation device applies the selected scatter model, to generate scatter-distribution data, using the projection data and the parameters as inputs.

The flow then proceeds to block B640, where the image-generation device generates corrected projection data based on the projection data and on the scatter-distribution data. The flow then advances to block B645, where the image-generation device generates second radiographic-image data (corrected radiographic-image data), which define one or more second reconstructed images (one or more corrected reconstructed images), based on the corrected projection data. Next, in block B650, the image-generation device outputs the second radiographic-image data to a display device.

Finally, the flow ends in block B655.

FIG. 7 illustrates the flow of information in an example embodiment of a training process. Preprocessing operations 1601A-C are performed on projection data 1010 (e.g., sets of projection data 1010) and corresponding radiographic-image data 1101 (radiographic-image data 1101 generated from the corresponding projection data 1010) from a training dataset 700. The projection data 1010 from a scanning operation may be stored together in a projection dataset 703, and the corresponding radiographic-image data 1101 may be stored in a corresponding radiographic-image dataset 705. A large training dataset 700, which includes a plurality of projection datasets 703 and corresponding radiographic-image datasets 705, can be used to account for the several factors upon which X-ray scatter can depend, for example the following: scanning-device geometry (e.g., CT scanning-device geometry), the source energy spectrum, and the size and organ distribution of patients. Thus, in some embodiments, the training dataset 700 can include a plurality of phantom projection datasets 703 (and corresponding radiographic-image datasets 705) and a plurality of patient projection datasets 703 (and corresponding radiographic-image datasets 705). Each phantom of the plurality of phantom projection datasets 703 can be selected according to a pre-determined human anatomy through modulation of the shape, size, and material each phantom is constructed from. In addition, and in consideration of a representative population of patients, the plurality of patient projection datasets 703 can be selected to include patients of simple and complex anatomies, the data including typical patient data with variations including, among others, patient shape, patient anatomy, organ distribution, size, metal inclusion, and contrast. Also, the patient projection datasets 703 can be selected to include variations in the scanning kVp and dosage.

Also, each projection dataset 703 has corresponding target data 707. The corresponding target data 707 may define what the projection data from the corresponding projection dataset 703 would be if at least some of the scatter flux was removed. Thus, the corresponding target data 707 may define the primary flux of the corresponding projection data 703 while omitting some (e.g., all or almost all) or all of the scatter flux of the corresponding projection data 703. The neural networks 1501A-C are trained such that they output parameters 1103A-C that, when applied by the scatter model 1505, cause the scatter model 1505 to output scatter-distribution data 1105 that match the target data 707 as close as possible.

The corresponding target data 707 of a projection dataset 703 may define a scatter distribution (e.g., a total scatter distribution) on one or more radiation detectors. For example, in some embodiments, the specific intensity of photon flux at point r in a total scatter distribution may be described, in the format of a radiative transfer equation, as follows:

$$\psi(\vec{r},E,\hat{\Omega})=\int_{\vec{r}_c}\vec{dr'}\int\vec{d\Omega'}dE'f(\vec{r'},E,E',\hat{\Omega}\cdot\hat{\Omega}')\psi$$
$$(\vec{r'},E',\hat{\Omega}')\exp[-\int_{\vec{r'}}\vec{dr''}\mu(\vec{r''},E)]+\psi_c$$
$$(\vec{r}_c,E,\hat{\Omega})\exp[-\int_{\vec{r}_c}\vec{dr''}\mu(\vec{r''},E)], \quad (2)$$

where $\psi(\hat{r}, E, \hat{\Omega})$ is the specific intensity of photon flux at point $\hat{r}$, energy E, and direction $\hat{\Omega}$; where $\psi_c(\vec{r}_c, E, \hat{\Omega})$ depends on the X-ray source and bowtie scattering; where $\vec{r}_c$ indicates a point on the surface of the object; where $\hat{n}$ is the normal direction of the boundary surface; where $f(\vec{r}', E, E', \hat{\Omega}\cdot\hat{\Omega}')$ is the scatter cross section, for x-ray CT, Compton, and Rayleigh scattering; and where $\mu(\vec{r}'', E)$ is the total attenuation coefficient.

During training, preprocessing operations 1601A-C are performed on projection data 1010 (from a respective projection dataset 703) and corresponding radiographic-image data 1101 (from a respective radiographic-image dataset 705). In this embodiment, preprocessing 1 (1601A) is performed on the radiographic-image data 1101, and preprocessing 2 (1601B) through preprocessing N (1601C), where N is a positive integer greater than 2 (e.g., 3, 4, 5, 10, 15), are performed on the projection data 1010. In other embodiments, more than one preprocessing operation is performed on the radiographic-image data 1101. Also, in some embodiments, the outputs of more than one preprocessing operation are input into the scatter model 1505. And, in some embodiments, the outputs of every preprocessing operation that accepts the projection data 1010 as inputs are input into at least one of the neural networks 1501A-C.

The neural networks 1501A-C accept, as inputs, the outputs of at least some of the preprocessing operations 1601A-C. Depending on the embodiment, each of the neural networks 1501A-C may accept the output of only one of the preprocessing operations 1601A-C, and each of the neural networks 1501A-C may accept the outputs of two or more of the preprocessing operations 1601A-C. For example, in FIG. 7, neural network 1 (1501A) may accept, as inputs, the outputs of one or both of preprocessing 1 (1601A) and preprocessing 2 (1601B), and neural network 2 (1501B) may accept, as inputs, the outputs of one or both of preprocessing 1 (1601A) and preprocessing 2 (1601B).

Each of the neural networks 1501A-C outputs a respective parameter or respective parameters of the parameters 1103A-C. Also, each parameter 1103A-C (e.g., each of the parameters in equation (1)) that is input into the scatter model 1505 may be output by one, and only one, of the neural networks 1501A-C.

The parameters 1103A-C and the output of preprocessing N (1601C) are input to the scatter model 1505, which outputs scatter-distribution data 1105. In some embodiments, the scatter-distribution data 1105 (S(view, c, r)) can be described by the following:

$$S(\text{view}, c, r) \approx \qquad (3)$$
$$([I_0(c, r)C_1(c, r)(-P(\text{view}, c, r)\ln P(\text{view}, c, r))] \otimes [G_0(c, r)]) \times \frac{C_2(c, r)}{I_0(c, r)},$$

where $C_1$ and $C_2$ are coefficients that depend on scan geometry, and where $I_0$ is the incident air count after the bow-tie filter. PlnP, which may be a forward scatter model, may describe preprocessing 1 (1601A) and preprocessing 2 (1601B). And $G_0(c,r)$ may be described by equation (1).

The scatter-distribution data 1105 and the target data 707 are input into one or more loss functions 1601. Some embodiments include only one loss function 1601, and some embodiments include multiple loss function 1601. For example, some embodiments include a respective loss function 1601 for each of the neural networks 1501A-C, and some embodiments include a respective loss function 1601 for a subset of the neural networks 1501A-C (e.g., a respective loss function 1601 for neural networks 1 and 2 (1501A-B) and a respective loss function 1601 for neural network N (1501C)). Thus, a loss function may have only one corresponding neural network, and a loss function may have multiple corresponding neural networks.

The one or more loss functions 1601 output respective loss values 1605, which are gradients in this embodiment, based on the scatter-distribution data 1105 and the target data 707. The respective loss values 1605 (e.g., gradients) are backpropagated through the scatter model 1505 (which is differentiable) and then through their corresponding neural networks 1501A-C. For example, if each of the neural networks 1501A-C has a respective corresponding loss function 1601, then the respective loss value 1605 of each loss function 1601 is backpropagated through the scatter model 1505 and then through the respective corresponding neural network (of the neural networks 1501A-C) of the loss function 1601.

For example, the backpropagation may use one or more of the following: a steepest descent method (e.g., with variable learning rate, with variable learning rate and momentum, and resilient backpropagation), a quasi-Newton method (e.g., Broyden-Fletcher-Goldfarb-Shanno, one step secant, and Levenberg-Marquardt), or a conjugate gradient method (e.g., Fletcher-Reeves update, Polak-Ribiere update, Powell-Beale restart, and scaled conjugate gradient). And the optimization method by which the backpropagation is performed can use one or more of gradient descent, batch gradient descent, stochastic gradient descent, and mini-batch stochastic gradient descent. Additionally, the optimization method can be accelerated using one or more momentum update techniques in the optimization approach that results in faster convergence rates of stochastic gradient descent in deep networks, including, for example, a Nesterov momentum technique or an adaptive method, such as an Adagrad sub-gradient method, an Adadelta or RMSProp parameter update variation of the Adagrad method, and an Adam adaptive optimization technique. The optimization method can also apply a second order method by incorporating the Jacobian matrix into an update step.

After the backpropagation is finished, the training process in FIG. 7 can be repeated. The training process can be repeated until predefined stopping criteria, which are used to determine whether the training of the one or more neural networks 1501A-C is complete, are satisfied. For example, the predefined stopping criteria can evaluate whether the new error (e.g., loss value) or the total number of iterations performed exceed predefined values. For example, the stopping criteria can be satisfied if either the new error falls below a predefined threshold or if a maximum number of iterations are reached.

FIG. 8 illustrates an example embodiment of a neural-network training process. The flow begins in block B800 and then moves to block B805, where an image-generation device obtains a training dataset, one or more neural networks, and a scatter model. Next, in block B810, the image-generation device selects a projection dataset, a radiographic-image dataset, and target data from the training dataset. The projection dataset, the radiographic-image dataset, and the target data correspond to each other.

The flow then moves to block B815, where the image-generation device performs preprocessing on projection data (raw projection data) from the projection dataset or on radiographic-image data (raw projection data) from the radiographic-image dataset. The flow then advances to block B820, where the image-generation device applies one or more neural networks, using the raw projection data or the preprocessed projection data and using the raw radiographic-image data or the preprocessed radiographic-image data as inputs, to generate one or more parameters for the scatter model.

Next, in block B825, the image-generation device applies the scatter model, using the one or more parameters and using the raw projection data or the preprocessed projection data as inputs, to generate scatter-distribution data.

The flow then moves to block B830, where the image-generation device applies one or more loss functions, using the target data and the scatter-distribution data as inputs, to generate one or more gradients. Each loss function may correspond to one or more of the neural networks, although each neural network corresponds to only one loss function. Also, each gradient may correspond to one or more of the neural networks, although each neural network corresponds to only one gradient.

Next, in block B835, the image-generation device backpropagates the one or more gradients through the scatter model and then their through their corresponding neural networks of the one or more neural networks.

Then, in block B840, the image-generation device determines if the training of the one or more neural networks is finished (e.g., if predefined stopping criteria are satisfied). If the image-generation device determines that the training of the one or more neural networks is not finished (B840=No), then the flow returns to block B810, where the image-generation device selects a projection dataset, a radiographic-image dataset, and target data from the training dataset. The selected projection dataset, radiographic-image dataset, and target data may or may not have been previously selected. If the image-generation device determines that the training of the one or more neural networks is finished (B840=Yes), then the flow proceeds to block B845, where the image-generation device stores or outputs the one or more trained neural networks, and the flow ends.

FIG. 9 illustrates an example embodiment of a neural-network training process. The flow starts in block B900 and then moves to block B905, where an image-generation device obtains a training dataset, N neural networks (where N is a positive integer), a scatter model, and L loss functions (where L is a positive integer). The flow then advances to block B910, where the image-generation device sets a network index n to 1 (n=1) and sets a loss-function index i to 1 (i=1).

The flow then proceeds to block B915, where the image-generation device selects a projection dataset, a radiographic-image dataset, and target data from the training dataset. The projection dataset, the radiographic-image dataset, and the target data correspond to each other. The flow then moves to block B920, where the image-generation device performs preprocessing on projection data (raw projection data) from the projection dataset or on radiographic-image data (raw radiographic-image data) from the radiographic-image dataset. The flow then advances to block B925, where the image-generation device applies neural network n, using the raw projection data or the preprocessed projection data and using the raw radiographic-image data or the preprocessed radiographic-image data as inputs, to generate one or more parameters for the scatter model.

The flow then moves to block B930, where the image-generation device determines whether to apply another neural network (e.g., whether n<N). If the image-generation device determines to apply another neural network (B930=Yes), then the flow proceeds to block B935, where the image-generation device increases the network index n by 1 (e.g., n=n+1), and then the flow returns to block B925. If the image-generation device determines not to apply another neural network (B930=No), then the flow moves to block B940.

In block B940, the image-generation device applies the scatter model, using the generated parameters and using the raw projection data or the preprocessed projection data as inputs, to generate scatter-distribution data.

The flow then moves to block B945, where the image-generation device applies loss function i, using the target data and the scatter-distribution data as inputs, to generate gradient i (which is an example of a loss value). Each loss function may correspond to one or more of the neural networks, although each neural network corresponds to only one loss function. Also, each gradient may correspond to one or more of the neural networks, although each neural network corresponds to only one gradient. Next, in block B950, the image-generation device backpropagates gradient i through the scatter model and then through any neural networks that correspond to loss function i.

The flow then advances to block B955, where the image-generation device determines whether to apply another loss function (e.g., whether i<L). If the image-generation device determines to apply another loss function (B955=Yes), then the flow proceeds to block B960, where the image-generation device increases the loss-function index i by 1 (e.g., i=i+1), and then the flow returns to block B945. If the image-generation device determines not to apply another loss function (B955=No), then the flow moves to block B965.

Then, in block B965, the image-generation device determines whether the training of the one or more neural networks is finished (e.g., whether one or more predefined stopping criteria are satisfied). If the image-generation device determines that the training of the one or more neural networks is not finished (B965=No), then the flow returns to block B910. If the image-generation device determines that the training of the one or more neural networks is finished (B965=Yes), then the flow proceeds to block B970, where the image-generation device stores or outputs the one or more trained neural networks, and the flow ends.

Figure 10:
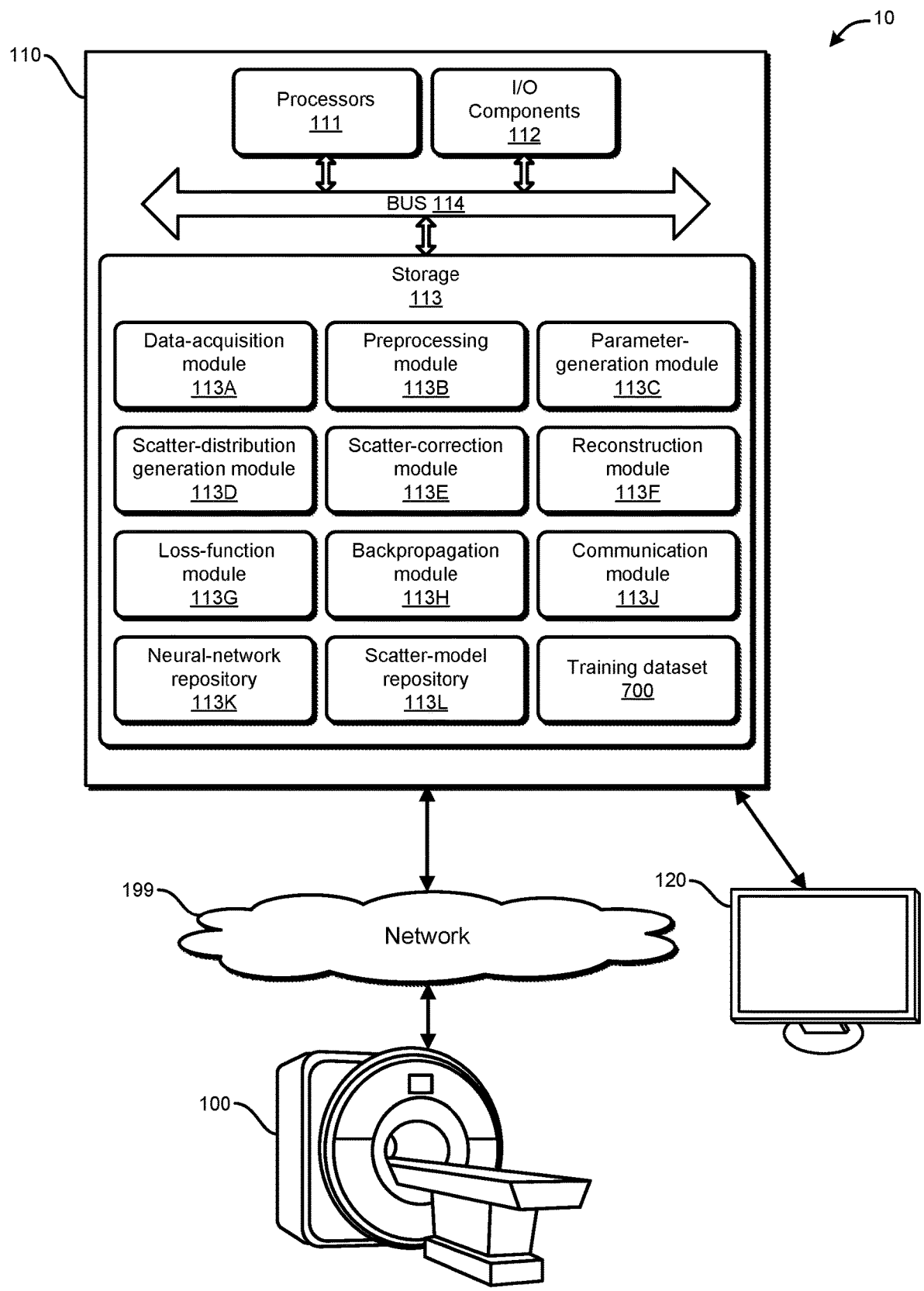
FIG. 10 illustrates an example embodiment of a medical-imaging system.

FIG. 10 illustrates an example embodiment of a medical-imaging system. The medical-imaging system 10 includes an image-generation device 110, which is a specially-configured computing device; a scanning device 100; and a display device 120. In this embodiment, the image-generation device 110 and the scanning device 100 communicate via one or more networks 199, which may include a wired network, a wireless network, a LAN, a WAN, a MAN, and a PAN. Also, in some embodiments the devices communicate via other wired or wireless channels.

The image-generation device 110 includes one or more processors 111, one or more I/O components 112, and storage 113. Also, the hardware components of the image-generation device 110 communicate via one or more buses 114 or other electrical connections. Examples of buses 114 include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 111 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The I/O components 112 include communication components (e.g., a GPU, a network-interface controller) that communicate with the display device 120, the scanning device 100, the network 199, and other input or output devices (not illustrated), which may include a keyboard, a mouse, a printing device, a touch screen, a light pen, an optical-storage device, a scanner, a microphone, a drive, a joystick, and a control pad.

The storage 113 includes one or more computer-readable storage media. As used herein, a computer-readable storage medium refers to a computer-readable medium that includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). The storage 113, which may include both ROM and RAM, can store computer-readable data or computer-executable instructions.

The image-generation device 110 additionally includes a data-acquisition module 113A, a preprocessing module 113B, a parameter-generation module 113C, a scatter-distribution-generation module 113D, a scatter-correction module 113E, a reconstruction module 113F, a loss-function module 113G, a backpropagation module 113H, and a communication module 113J. A module includes logic, computer-readable data, or computer-executable instructions. In the embodiment shown in FIG. 10, the modules are implemented in software (e.g., Assembly, C, C++, C#, Java, BASIC, Perl, Visual Basic). However, in some embodiments, the modules are implemented in hardware (e.g., customized circuitry) or, alternatively, a combination of software and hardware. When the modules are implemented, at least in part, in software, then the software can be stored in the storage 113. Also, in some embodiments, the image-generation device 110 includes additional or fewer modules, the modules are combined into fewer modules, or the modules are divided into more modules. Furthermore, the storage 113 includes a neural-network repository 113K, which stores neural networks (or other machine-learning models); a scatter-model repository 113L, which stores scatter models; and a training dataset 700.

The data-acquisition module 113A includes instructions that cause the image-generation device 110 to acquire projection data, for example from the scanning device 100 or from an external device (e.g., a storage device that communicates via the network 199). For example, some embodiments of the data-acquisition module 113A include instructions that cause the image-generation device 110 to perform at least some of the operations that are described in block B410 in FIG. 4, in block B505 in FIG. 5, and in block B605 in FIG. 6.

The preprocessing module 113B includes instructions that cause the image-generation device 110 to perform preprocessing operations on projection data or on radiographic-image data. For example, some embodiments of the preprocessing module 113B include instructions that cause the image-generation device 110 to perform at least some of the operations that are described in block B615 in FIG. 6, in block B815 in FIG. 8, and in block B920 in FIG. 9.

The parameter-generation module 113C includes instructions that cause the image-generation device 110 to generate parameters for a scatter model by applying one or more neural networks (or other machine-learning models), using projection data (e.g., raw projection data, preprocessed projection data) and radiographic-image data (e.g., raw radiographic-image data, preprocessed radiographic-image data) as inputs. For example, some embodiments of the parameter-generation module 113C include instructions that cause the image-generation device 110 to perform at least some of the operations that are described in block B430 in FIG. 4, in block B525 in FIG. 5, in block B630 in FIG. 6, in block B820 in FIG. 8, and in block B925 in FIG. 9.

The scatter-distribution-generation module 113D includes instructions that cause the image-generation device 110 to generate scatter-distribution data by applying one or more scatter models, using projection data (e.g., raw projection data, preprocessed projection data) and generated parameters as inputs. For example, some embodiments of the scatter-distribution-generation module 113D include instructions that cause the image-generation device 110 to perform at least some of the operations that are described in block B440 in FIG. 4, in block B530 in FIG. 5, in block B635 in FIG. 6, in block B825 in FIG. 8, and in block B940 in FIG. 9.

The scatter-correction module 113E includes instructions that cause the image-generation device 110 to generate corrected projection data based on projection data (e.g., raw projection data, preprocessed projection data) and on scatter-distribution data. For example, some embodiments of the scatter-correction module 113E include instructions that cause the image-generation device 110 to perform at least some of the operations that are described in block B450 in FIG. 4, in block B535 in FIG. 5, and in block B640 in FIG. 6.

The reconstruction module 113F includes instructions that cause the image-generation device 110 to generate radiographic-image data (e.g., corrected radiographic-image data) based on projection data (e.g., corrected projection data). For example, some embodiments of the reconstruction module 113F include instructions that cause the image-generation device 110 to perform at least some of the operations that are described in blocks B420 and B460 in FIG. 4, in blocks B510 and B540 in FIG. 5, and in blocks B610 and B645 in FIG. 6.

The loss-function module 113G includes instructions that cause the image-generation device 110 to calculate loss values (e.g., gradients) of loss functions based on scatter-distribution data and on target data. For example, some embodiments of the loss-function module 113G include instructions that cause the image-generation device 110 to perform at least some of the operations that are described in block B830 in FIG. 8 and in block B945 in FIG. 9.

The backpropagation module 113H includes instructions that cause the image-generation device 110 to backpropagate loss values (e.g., gradients) through scatter models and neural networks (e.g., to modify the neural networks) and to determine whether neural-network training has been completed. For example, some embodiments of the backpropagation module 113H include instructions that cause the image-generation device 110 to perform at least some of the operations that are described in blocks B835-B840 in FIG. 8 and in blocks B950-B965 in FIG. 9.

The communication module 113J includes instructions that cause the image-generation device 110 to communicate with other devices, including the scanning device 100 and external storage devices (which may store datasets).

Also, some embodiments of the image-generation device 110 omit the loss-function module 113G, the backpropagation module 113H, and the training dataset 700, and thus do not train the neural networks.

The scope of the claims is not limited to the above-described embodiments and includes various modifications and equivalent arrangements.

The invention claimed is:

1. A data processing method for scatter correction, the data processing method comprising:
   obtaining first radiographic image data reconstructed based on a set of projection data acquired in a radiographic scan;
   applying one or more trained machine-learning models to the set of projection data and the first radiographic image data to obtain a set of parameters for a scatter kernel;
   inputting the set of parameters and the set of projection data into the scatter kernel to obtain scatter-distribution data; and
   performing scatter correction on the set of projection data using the scatter-distribution data, to obtain a set of corrected projection data.

2. The data processing method of claim 1, further comprising:
   reconstructing a second radiographic image from the set of corrected projection data.

3. The data processing method of claim 2, further comprising:
   outputting the second radiographic image for display.

4. The data processing method of claim 1, wherein the set of projection data are computed-tomography (CT) data,
   wherein the set of corrected projection data are CT data, and
   wherein the radiographic scan is an X-ray CT scan.

5. The data processing method of claim 1, wherein the scatter kernel is a convolutional kernel.

6. The data processing method of claim 1, wherein the one or more trained machine-learning models are neural networks.

7. The data processing method of claim 1, wherein the set of parameters includes parameters that depend on scanned geometry, equivalent monochromatic energy, an anti-scatter grid, and one or more scanned materials.

8. A method for training one or more machine-learning models, the method comprising:
   obtaining a training dataset for a scatter model, wherein the training dataset includes projection data, radiographic-image data, and target data, wherein the target data define a scatter distribution, and wherein the scatter model accepts, as inputs, a set of parameters and projection data;
   applying the projection data and the radiographic-image data to one or more machine-learning models to generate the set of parameters for the scatter model;
   using the scatter model to generate, based on the set of parameters and on the projection data, output scatter-distribution data;
   applying the output scatter-distribution data and the target data to a loss function to obtain a loss value; and
   updating the one or more machine-learning models based on the loss value.

9. The method of claim 8, wherein each of the one or more machine-learning models is a respective neural network.

10. The method of claim 8, wherein the target data define a scatter distribution.

11. The method of claim 8, wherein obtaining the training dataset includes:
    obtaining raw projection data and raw radiographic-image data;
    performing first preprocessing on the raw radiographic-image data to generate the radiographic-image data; and
    performing second preprocessing on the raw projection data to generate the projection data.

12. The method of claim 8, wherein the one or more machine-learning models include at least two machine-learning models, and
    wherein each machine-learning model of the at least two machine-learning models outputs one or more respective parameters of the set of parameters for the scatter model.

13. The method of claim 8, wherein the loss value is a gradient of the loss function.

14. The method of claim 8, wherein the scatter model is a convolutional kernel.

15. An information processing apparatus comprising:
one or more computer-readable storage media; and
one or more processors, wherein the one or more processors cooperate with the one or more computer-readable storage media to cause the information processing apparatus to
obtain first radiographic-image data reconstructed based on a set of projection data acquired in a radiographic scan;
apply one or more trained machine-learning models to the set of projection data and the first radiographic-image data to obtain a set of parameters for a scatter model;
apply the scatter model, using the set of parameters and the set of projection data as inputs, to obtain scatter-distribution data; and
perform scatter correction on the set of projection data using the scatter-distribution data, to obtain a set of corrected projection data.

16. The information processing apparatus of claim 15, wherein the one or more trained machine-learning models are neural networks.

17. The information processing apparatus of claim 15, wherein the set of parameters includes parameters that depend on scanned geometry, equivalent monochromatic energy, an anti-scatter grid, and one or more scanned materials.

18. The information processing apparatus of claim 15, wherein the one or more processors cooperate with the one or more computer-readable storage media to further cause the information processing apparatus to
reconstruct a second radiographic image from the set of corrected projection data.

19. The information processing apparatus of claim 15,
wherein the one or more trained machine-learning models include a first trained machine-learning model that accepts both projection data and radiographic-image data as inputs.

20. The information processing apparatus of claim 15,
wherein the one or more trained machine-learning models include a first trained machine-learning model that accepts projection data, but not radiographic-image data, as inputs; and
wherein the one or more trained machine-learning models include a second trained machine-learning model that accepts radiographic-image data, but not projection data, as inputs.

* * * * *